United States Patent [19]

Arick

[11] Patent Number: 5,681,323
[45] Date of Patent: Oct. 28, 1997

[54] EMERGENCY CRICOTHYROTOMY TUBE INSERTION

[76] Inventor: Daniel S. Arick, 20 W. 64th St., Apt. 17D, New York, N.Y. 10023

[21] Appl. No.: 680,382

[22] Filed: Jul. 15, 1996

[51] Int. Cl.⁶ .................................................. A61F 11/00
[52] U.S. Cl. ........................................ 606/108; 606/185
[58] Field of Search ............................... 606/1, 108, 167, 606/181, 182, 184, 185, 188; 604/164, 264, 272; 128/749-754

[56] References Cited

U.S. PATENT DOCUMENTS 3,888,258   6/1975   Akiyama ............................... 606/109
4,969,454   11/1990  Servello ............................... 606/185
5,242,427   9/1993   Bilweis ............................... 606/185

*Primary Examiner*—Glenn Dawson
*Attorney, Agent, or Firm*—McAulay Fisher Nissen Goldberg & Kiel, LLP

[57] ABSTRACT

The present invention is drawn to a criocthyrotomy tube insertion device which provides for the accurate delivery and placement of a cricothyrotomy tube. The force applied to insert the cricothyrotomy tube and the duration of the application of the force are predetermined to assure safe and accurate insertion of the cricothyrotomy tube. The device is easily positioned to ensure deliver of the cricothyrotomy tube in the crico-thyroid region.

22 Claims, 3 Drawing Sheets

EMERGENCY CRICOTHYROTOMY TUBE INSERTION

BACKGROUND

The present invention relates to emergency medical care and more particularly to the insertion of a cricothyrotomy tube.

There are currently two commonly used methods for providing an emergency airway for a patient suffering from respiratory distress: intubation and cricothyrotomy. The emergency airway must be established within a few minutes before the risk of permanent brain damage or death becomes significant. This usually greatly raises the anxiety level of the person attempting to secure the emergency airway.

Intubation is a procedure whereby a tube is inserted through the patient's mouth and is passed between the patient's vocal cords to provide an airway to the patient.

A cricothyrotomy is a more severe procedure where an incision is made into the anterior trachea, normally in the area of the crico-thyroid membrane, and a tube is inserted into the incision to provide an airway for the patient. Ordinarily, the cricothyrotomy is a last resort and is not employed unless intubation fails. Since intubation is attempted prior to the cricothyrotomy and since oxygen has not been available to the patient for some period of time, it is important that the cricothyrotomy be done quickly and correctly to provide an operable airway.

The cricothyrotomy is performed manually using one of two procedures. First, the crico-thyroid membrane is located by feeling the throat of the patient and locating the region at the base of the patient's Adam's apple. If available, a scalpel is used to cut the tissue in the crico thyroid membrane and the cricothyrotomy tube is inserted. This is a surgical procedure.

Second, emergency insertion devices have been developed where a trochar is inserted into the cricothyrotomy tube and the trochar and cricothyrotomy tube are simultaneously and manually inserted into the patient without a previously made incision. This is a non-surgical procedure.

The problem with the surgical procedure is that the incision can result in bleeding and collapse of soft tissue which can complicate the later insertion of the cricothyrotomy tube. In addition, the surgical procedure is a multi-step procedure requiring first, an incision; second, holding the incision open with a clamp; third, simultaneously inserting of a tube and blunt inner cannula; and forth, removal of the blunt inner cannula.

The non-surgical procedure suffers from inconsistent force and stroke of the insertion apparatus and tube. Since the force is manually applied, the amount and duration of the application of force is relatively unpredictable. In addition, the non-surgical devices are somewhat cumbersome to handle and do not provide structure for positioning the device prior to insertion.

Complications including failure to locate the appropriate location on the neck before attempting the cricothyrotomy, bleeding, anxiety associated with the emergency situation, and the unpredictable application of force magnify the need to improve the certainty with which the emergency cricothyrotomy is performed.

The present invention provides for an improvement in the installation of an emergency cricothyrotomy tube.

BRIEF DESCRIPTION

The present invention is drawn to a cricothyrotomy tube insertion device which provides for the accurate delivery and placement of a cricothyrotomy tube. The force applied to insert the cricothyrotomy tube and the duration of the application of the force are predetermined to assure safe and accurate insertion of the cricothyrotomy tube. The device is easily positioned to ensure instant and accurate delivery of the cricothyrotomy tube in the crico-thyroid region to provide an airway within seconds.

BRIEF DESCRIPTION OF THE DRAWINGS

FIG. 1 illustrates an apparatus for inserting a cricothyrotomy tube having the cricothyrotomy tube positioned relative to the apparatus. The apparatus illustrated in FIG. 1 occupies a non-cocked state.

FIG. 2 is a view similar to FIG. 1, however, the apparatus has been cocked and positioned for delivery of the cricothyrotomy tube.

FIG. 3 is a view similar to FIG. 2, however, the apparatus has been discharged and is illustrated in the tissue piercing and cricothyrotomy tube delivering state.

FIG. 4 is a view similar to FIGS. 1–3, however, the apparatus is removed from the patient and the cricothyrotomy tube remains inserted in the patient.

DESCRIPTION OF THE PREFERRED EMBODIMENTS

Figure 1:
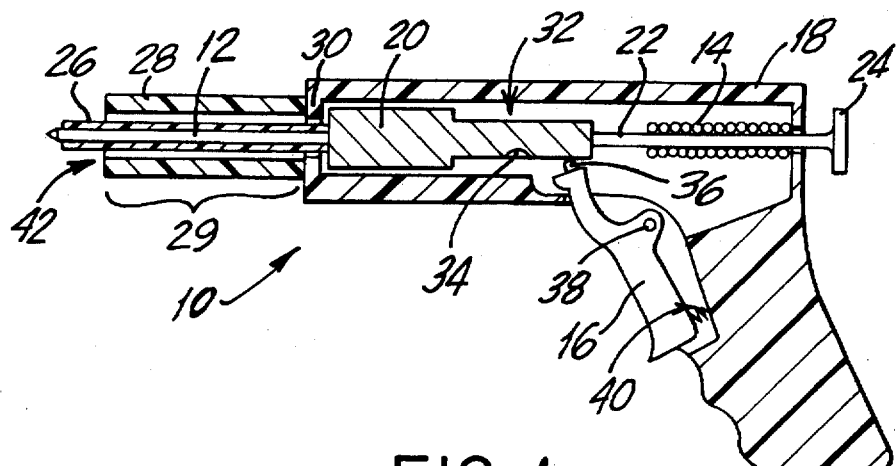
FIGS. 1 through 4 are longitudinal cross-sectional views which illustrate a series of states occupied by an apparatus for inserting a cricothyrotomy tube according to the present invention.

Referring to FIGS. 1 through 4, a cricothyrotomy tube insertion device 10 includes: sharp central trocar 12, translation mechanism 14, user-controlled activation element 16, and hand-held housing 18. Hand-held housing 18 directly or indirectly supports sharp central trocar 12, translation mechanism 14, and user-controlled activation element 16. When activation element 16 is activated, translation mechanism 14 propels sharp central trocar 12 forward.

In the embodiment illustrated in each of FIGS. 1 through 4, proximal end of sharp central trocar 12 is connected to piston 20, proximal end of piston 20 is connected to rod 22, and rod 22 is positioned between piston 20 and cap 24. Translation mechanism 14 is constructed as a spring and is positioned around rod 22 within housing 18.

Positioning element 28 is positioned at the distal end of housing 18 and surrounds cricothyrotomy tube 26 which, in turn, surrounds sharp central trocar 12. Longitudinal bore 42 of positioning element 28 permits movement of sharp central trocar 12 and cricothyrotomy tube 26 relative to positioning element 28. In addition, opening 30 in the distal end of housing 18 permits the movement of sharp central trocar 12 and cricothyrotomy tube 26 relative to housing 18. At least a portion of piston 20 is moveable within cavity 32 of device 10.

Activation element 16 pivots relative to housing 18 about point 38 and is biased by spring 40. Piston 20 provides recess 34 which is adapted to mate with protrusion 36 of activation element 16. Spring 40 biases protrusion 36 toward piston 20 to encourage engagement of protrusion 36 with recess 34.

As illustrated in FIG. 1, device 10 for inserting cricothyrotomy tube 26 occupies the non-cooked state. Translation mechanism 14 is at rest and is not in condition to propel sharp central trocar 12 forward.

Figure 2:
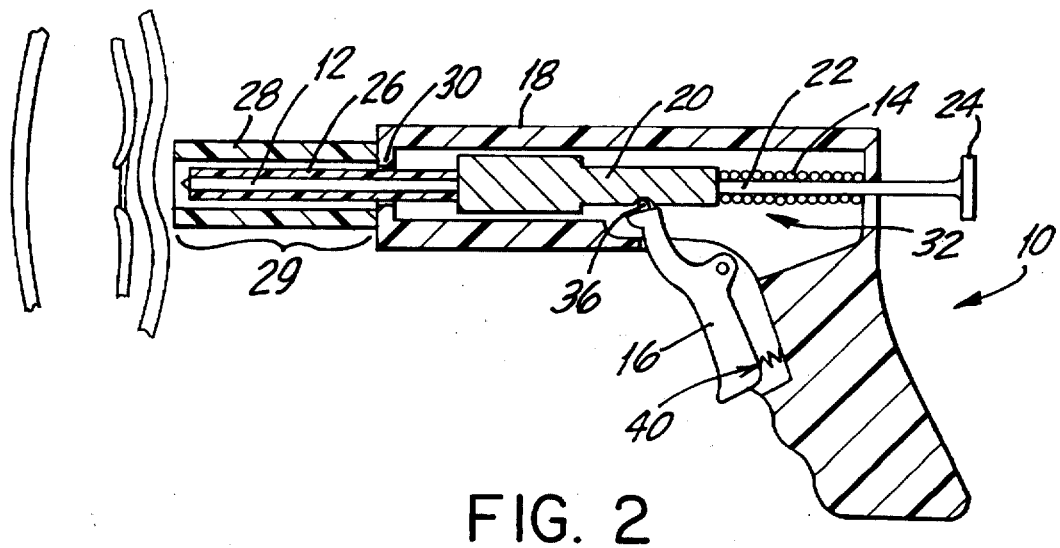

Referring to FIG. 2, device 10 occupies the cocked state and is positioned adjacent to the crico-thyroid region of a patient. Device 10 is prepared for propelling sharp central trocar 12 forward.

The user retracts piston 20 from the state illustrated in FIG. 1 by holding housing 18 and pulling cap 24 to compress translation mechanism 14 about rod 22 between housing 18 and piston 20 until protrusion 36 engages recess 34 of piston 20. Once protrusion 36 engages recess 34, no further retraction of piston 20 is necessary. Spring 40 biases activation element 16 so that protrusion 36 engages recess 34 when recess 34 is positioned adjacent to protrusion 36. Preferably, sharp central trocar 12 and cricothyrotomy tube 26 do not extend beyond the distal end of positioning element 28 when device 10 occupies the cocked state. Preferably, the length of sharp central trocar 12 is greater than that of cricothyrotomy tube 26 so that the distal end of sharp central trocar 12 extends beyond the distal end of cricothyrotomy tube 26 when cricothyrotomy tube 26 occupies its most retracted state.

Preferably, while occupying the cocked state illustrated in FIG. 2, the distal end of positioning element 28 is pressed against the patient in the crico-thyroid region to position sharp central trocar 12 and cricothyrotomy tube 26 for insertion. The distal end of positioning element 28, when pressed against the patient, stabilizes device 10. Preferably, positioning element 28 provides viewing zone 29 to facilitate accurate positioning of device 10 prior to activation. Viewing zone 29 may be constructed from a transparent material such as Lucite. In one embodiment, positioning element 28 may be constructed from transparent material so that viewing zone 29 covers the entire surface area of positioning element 28. Viewing zone 29 permits the user to align the expected travel of trocar 12 and cricothyrotomy tube 26 with the crico-thyroid region of the patient to facilitate accurate insertion of cricothyrotomy tube 26.

Figure 3:
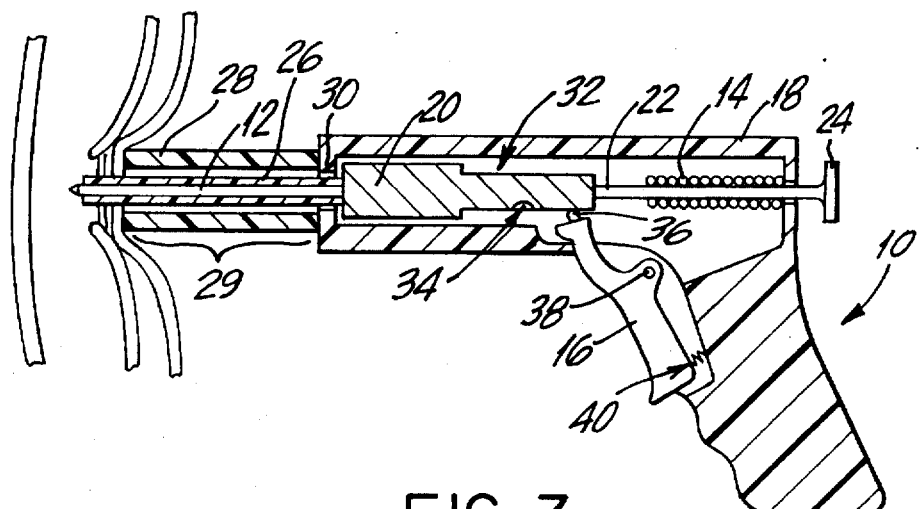

Referring to FIG. 3, activation element 16 has been activated by the user. Translation mechanism 14 forces piston 20 forward, which in turn, causes rapid forward motion of sharp central trocar 12 and cricothyrotomy tube 26. Preferably, sharp central trocar 12 and cricothyrotomy tube 26 are forced to a position so that at least a portion of sharp central trocar 12 and of cricothyrotomy tube 26 extend from the distal end of positioning element 28. The depth of penetration of sharp central trocar 12 is limited by the contact between piston 20 and housing 18 as well as the length of positioning element 28.

The user activates activation element 16 by causing movement of protrusion 36 to disengage from recess 34. Movement of protrusion 36 is accomplished by exceeding the spring force associated with spring 40 to cause activation element 16 to pivot so as to cause the desired disengagement. Upon disengagement, translation mechanism 14 forces piston 20 forward with a predetermined force which in turn causes sharp central trocar 12 and cricothyrotomy tube 26 to translate forward. Preferably, positioning element 28 is pressed against the patient in the crico-thyroid region during activation to cause sharp central trocar 12 to pierce the tissue and cricothyrotomy tube 26 to extend into the opening created by sharp central trocar 12. Preferably, concurrent movement of sharp central trocar 12 and cricothyrotomy tube 26 is caused by activating the translation mechanism 14. The travel of sharp central trocar 12 is limited by contact of piston 20 with housing 18.

The length of positioning element 28 may be modified so as to provide a different depth of insertion of sharp central trocar 12 and cricothyrotomy tube 26. More specifically, a shorter positioning element 28 causes deeper insertion and penetration of sharp central trocar 12 and cricothyrotomy tube 26. In contrast, a longer positioning element 28 minimizes the penetration and depth of insertion of sharp central trocar 12 and cricothyrotomy tube 26.

Figure 4:
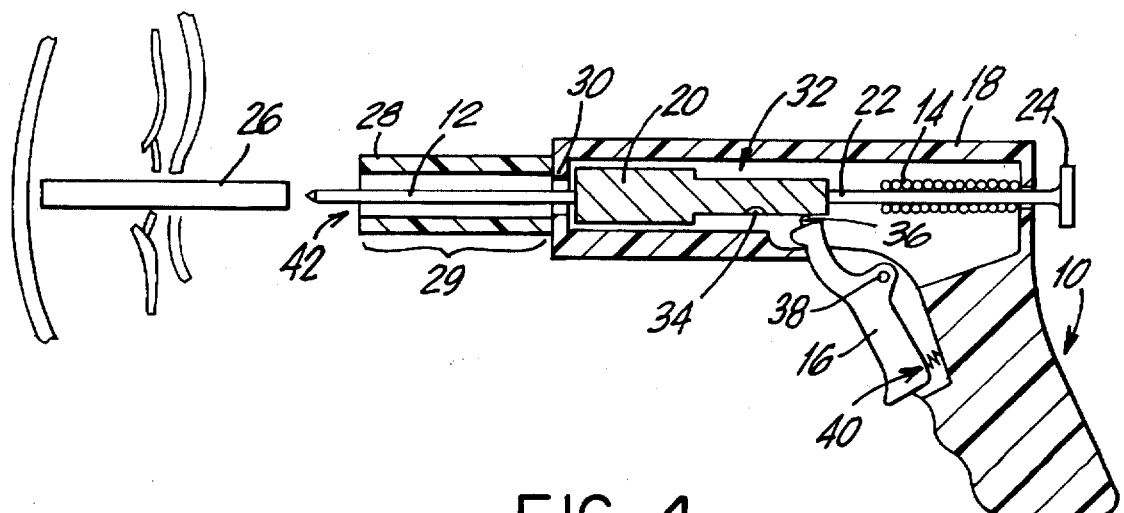
Figure 5:
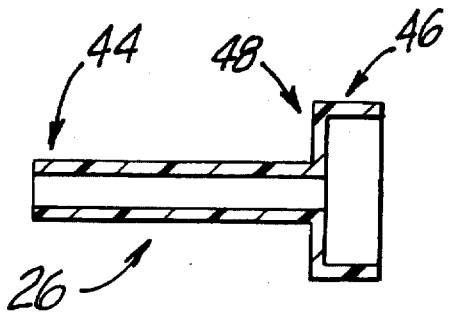
FIG. 5 through 10 are longitudinal cross-sectional views of alternative cricothyrotomy tubes for use with the apparatus illustrated in FIGS. 1 through 4.
Figure 6:
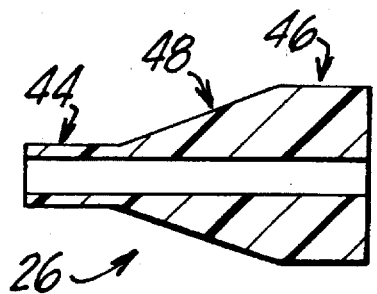
Figure 7:
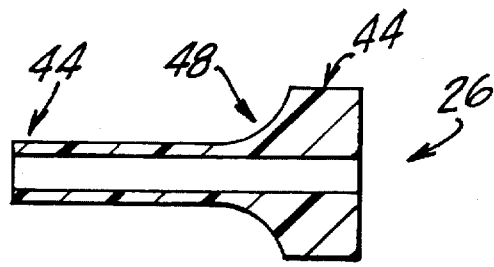
Figure 8:
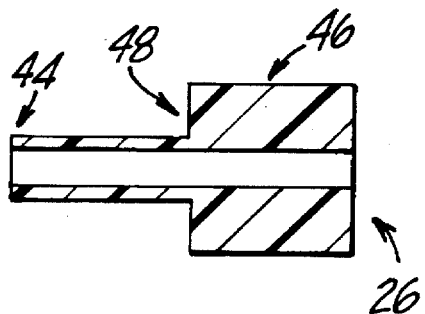
Figure 9:
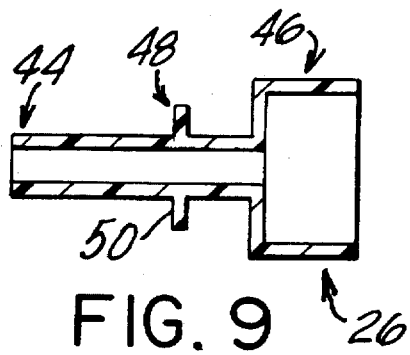
Figure 10:
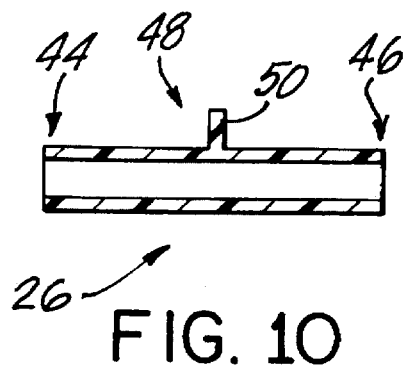

Referring to FIG. 4, after cricothyrotomy tube 26 has been inserted into the crico-thyroid region of a patient, device 10 is removed by sliding device 10 along the longitudinal axis of cricothyrotomy tube 26. To facilitate removal, the user may hold cricothyrotomy tube 26 in place while withdrawing device 10.

In one embodiment of the device, translation mechanism 14 is a 20 pound spring and the cricothyrotomy tube 26 has an outer distal diameter of approximately 0.5 cm. The trochar and cricothyrotomy tube extend approximately 3.0 cm and approximately 2.5 cm, respectively, past the distal end of positioning element 28 at completion of insertion.

Referring to FIGS. 5 through 10, cricothyrotomy tube 26 may be constructed having outer distal diameter 44 and outer proximal diameter 46. Preferably, outer proximal diameter 46 is approximately 1.5 cm to accommodate connecting to standard ventilating equipment, including an ambu bag. In addition, cricothyrotomy tube 26 may provide insertion depth limiting region 48 to prevent over-insertion of cricothyrotomy tube 26. Insertion depth limiting region 48 may be the area of transition from distal constructed as an additional protrusion or shoulder 50.

While device 10 has been illustrated in the figures as having a handle and trigger-shaped construction, it is understood that this invention may be made as a linear device having an overall shape similar to a syringe where the activation element is positioned for finger or thumb access by the user and the device facilitates one-handed operation. In addition, recess 34 on piston 20 may be replaced with a series of recesses to provide a force selection element to permit the user to choose from a number of predetermined forces which may be applied by translation mechanism 14.

While a number of embodiments have been described having specific features, it is not beyond the scope of the present invention that any one or more features of one embodiment may be combined with any one or more features of other embodiments.

What is claimed is:

1. A device for inserting an emergency airway comprising:

a sharp central trocar for piercing tissue, said sharp central trocar supporting a cricothyrotomy tube;

a translation mechanism connected to said trocar for applying a predetermined distal force to said sharp central trocar for moving said sharp central trocar from a cocked state to a tissue-piercing state, said translation mechanism concurrently moving the cricothyrotomy tube supported by said sharp central trocar from a non-inserted state to an inserted state;

a user-controlled activation element for activating said translation mechanism to effect movement of said sharp central trocar and the cricothyrotomy tube; and, a hand-held housing supporting said sharp central trocar, said translation mechanism and said activation element;

said sharp central trocar and the cricothyrotomy tube adapted for use in a crico-thyroid region of a patient.

2. The device of claim 1 wherein the cricothyrotomy tube includes a longitudinal bore, said sharp central trocar slidably receiving said cricothyrotomy tube and said cricothyrotomy tube being removable from said sharp central trocar.

3. The device of claim 2 wherein said cricothyrotomy tube comprises a distal end and a proximal end, said distal end having an outer distal diameter and said proximal end having an outer proximal diameter.

4. The device of claim 3 wherein said outer proximal diameter is adapted to connect to standard ventilating equipment.

5. The device of claim 3 wherein said cricothyrotomy tube further comprises an insertion depth limiting region between said distal end and said proximal end.

6. The device of claim 5 wherein said insertion depth limiting region provides a shoulder having an outer diameter greater than said outer distal diameter.

7. The device of claim 1 wherein said housing comprises a positioning element.

8. The device of claim 7 wherein said positioning element provides a viewing zone.

9. The device of claim 7 wherein said trocar extends a predetermined distance from a distal end of said positioning element after said device occupies said tissue-piercing state.

10. The device of claim 1 wherein said translation mechanism comprises a spring.

11. The device of claim 1 further comprising a force selection element operatively connected to said trocar for preselecting said predetermined force.

12. A device for inserting an emergency airway comprising:

a hand-held housing having a distal opening, a sharp central trocar in said housing, said sharp central trocar supporting a cricothrotomy tube, said sharp central trocar being movable between a distal protracted position extending a predetermined distance distal of said distal opening of said housing and a proximal retracted position within said housing, a translation mechanism coupled to said cutting sharp central trocar, said translation mechanism having an active state in which said translation mechanism forces said sharp central trocar and said cricothyrotomy tube from said retracted position to said protracted position, an operator-controlled trigger operatively connected to said translation mechanism for initiating said active state of said translation mechanism, said distal opening of said housing being adapted to be placed over a crico-thyroid region of a patient.

13. The device of claim 12 wherein the cricothyrotomy tube, includes a longitudinal bore, said cricothyrotomy tube slidably receiving said sharp central trocar and being removable therefrom.

14. The device of claim 13 wherein said cricothyrotomy tube comprises a distal end and a proximal end, said distal end having an outer distal diameter and said proximal end having an outer proximal diameter.

15. The device of claim 14 wherein said outer proximal diameter is adapted to connect to standard ventilating equipment.

16. The device of claim 14 wherein said cricothyrotomy tube further comprises an insertion depth limiting region between said distal end and said proximal end.

17. The device of claim 16 wherein said insertion depth limiting region provides a shoulder having an outer diameter greater than said outer distal diameter.

18. The device of claim 12 wherein said housing comprises a positioning element.

19. The device of claim 18 wherein said positioning element provides a viewing zone.

20. The trocar claim 18 wherein said trocar extends a predetermined distance from a distal end of said positioning element after said device occupies said protracted position.

21. The device of claim 12 wherein said translation mechanism comprises a spring.

22. The device of claim 12 further comprising a force selection element operatively connected to said trocar for preselecting said predetermined force.

* * * * *